United States Patent
Malek et al.

(10) Patent No.: US 8,217,071 B2
(45) Date of Patent: Jul. 10, 2012

(54) USE OF INHIBITORS OF THE DEGRADATION OF P27, IN PARTICULAR ARGYRIN AND DERIVATIVES THEREOF, FOR THE TREATMENT OF PROLIFERATIVE DISEASES

(75) Inventors: Nisar Malek, Hannover (DE); Florenz Sasse, Braunschweig/Leiferde (DE); Irina Nickeleit, Barnstorf (DE); Roland Frank, Meine (DE); Bettina Hinkelmann, Braunschweig (DE); Heinrich Steinmetz, Hildesheim (DE)

(73) Assignees: Helmholtz Zentrum für Infektionsforschung GmbH, Braunschweig (DE); Medizinische Hochschule Hannover, Hannover (DE)

( * ) Notice: Subject to any disclaimer, the term of this patent is extended or adjusted under 35 U.S.C. 154(b) by 0 days.

(21) Appl. No.: 12/527,428

(22) PCT Filed: Feb. 27, 2008

(86) PCT No.: PCT/EP2008/001552
§ 371 (c)(1),
(2), (4) Date: Jan. 4, 2010

(87) PCT Pub. No.: WO2008/104387
PCT Pub. Date: Sep. 4, 2008

(65) Prior Publication Data
US 2010/0144822 A1    Jun. 10, 2010

Related U.S. Application Data

(60) Provisional application No. 60/965,932, filed on Aug. 22, 2007.

(30) Foreign Application Priority Data

Feb. 28, 2007  (EP) .................................. 07004185

(51) Int. Cl.
| | |
|---|---|
| *A01N 43/48* | (2006.01) |
| *A61K 31/40* | (2006.01) |
| *G01N 33/567* | (2006.01) |
| *G01N 33/574* | (2006.01) |

(52) U.S. Cl. ........................ 514/414; 435/7.21; 435/7.23
(58) Field of Classification Search ........................ None
See application file for complete search history.

(56) References Cited

U.S. PATENT DOCUMENTS

| 6,515,016 B2 * | 2/2003 | Hunter ............ 514/449 |
| 2002/0037919 A1 * | 3/2002 | Hunter ............ 514/449 |
| 2006/0035280 A1 | 2/2006 | Huang et al. |

FOREIGN PATENT DOCUMENTS

| GB | 2 367 553 | 4/2002 |
| WO | WO 02/055665 | 7/2002 |

OTHER PUBLICATIONS

Cohen, Phillip. The development and therapeutic potential of protein kinase inhibitors. Chemical Biology, 3 (1999), 459-465.*
Huff, Joel R. HIV Protease: A novel chemotherapeutic target for AIDS. Journal of Medicinal Chemistry, 34(8), 1991, 2305-2314.*
Golub et al. Science, 1999, vol. 286, 531-536.*
Lala et al. Cancer and Metastasis Reviews, 1998, 17(1): 91-106.*
Huang et al., "High-Throughput Screening for Inhibitors of the Cks1-Skp2 Interaction," *Methods in Enzymology*, 2005, vol. 399, pp. 717-728.

* cited by examiner

*Primary Examiner* — Brandon Fetterolf
*Assistant Examiner* — Anna Pagonakis
(74) *Attorney, Agent, or Firm* — Saliwanchik, Lloyd & Eisenschenk

(57) ABSTRACT

The present invention relates to the use of particular macrocycles that are inhibitors of the proteasomic degradation of p27, in particular Argyrin and derivatives thereof, preferably Argyrin A, for the treatment of proliferative diseases, such as cancer, as well as the derivatization of said macrocycles.

12 Claims, 8 Drawing Sheets a $C_{42}H_{46}N_{10}O_8S$
Mol. Wt.: 838.93 b a

SEQUENCE LISTING

```
<160> NUMBER OF SEQ ID NOS: 14

<210> SEQ ID NO 1
<211> LENGTH: 19
<212> TYPE: RNA
<213> ORGANISM: Homo sapiens

<400> SEQUENCE: 1
cguaaacagc ucgaauuaa                                              19

<210> SEQ ID NO 2
<211> LENGTH: 19
<212> TYPE: RNA
<213> ORGANISM: Homo sapiens

<400> SEQUENCE: 2
uuaauucgag cuguuuacg                                              19

<210> SEQ ID NO 3
<211> LENGTH: 19
<212> TYPE: RNA
<213> ORGANISM: Homo sapiens

<400> SEQUENCE: 3
ggauuuucaa uucauaccc                                              19

<210> SEQ ID NO 4
<211> LENGTH: 19
<212> TYPE: RNA
<213> ORGANISM: Homo sapiens

<400> SEQUENCE: 4
ggguaugaau ugaaaaucc                                              19

<210> SEQ ID NO 5
<211> LENGTH: 19
<212> TYPE: RNA
```

<213> ORGANISM: Homo sapiens

<400> SEQUENCE: 5
ggacgaucau gacaagaug                                                    19

<210> SEQ ID NO 6
<211> LENGTH: 19
<212> TYPE: RNA
<213> ORGANISM: Homo sapiens

<400> SEQUENCE: 6
caucuuguca ugaucgucc                                                    19

<210> SEQ ID NO 7
<211> LENGTH: 19
<212> TYPE: RNA
<213> ORGANISM: Homo sapiens

<400> SEQUENCE: 7
ggugcuuaua uugcuuccc                                                    19

<210> SEQ ID NO 8
<211> LENGTH: 20
<212> TYPE: RNA
<213> ORGANISM: Homo sapiens

<400> SEQUENCE: 8
gggaagcaau auaagcaccg                                                   20

<210> SEQ ID NO 9
<211> LENGTH: 19
<212> TYPE: RNA
<213> ORGANISM: Homo sapiens

<400> SEQUENCE: 9
gacugucuua cgcugacaa                                                    19

<210> SEQ ID NO 10
<211> LENGTH: 20
<212> TYPE: RNA
<213> ORGANISM: Homo sapiens

<400> SEQUENCE: 10
uugucagcgu aagacagucc                                                   20

<210> SEQ ID NO 11
<211> LENGTH: 19
<212> TYPE: RNA
<213> ORGANISM: Homo sapiens

<400> SEQUENCE: 11
gauauuacuc cuguguguu                                                    19

<210> SEQ ID NO 12
<211> LENGTH: 19
<212> TYPE: RNA
<213> ORGANISM: Homo sapiens

<400> SEQUENCE: 12
aacacacagg aguaauauc                                                    19

<210> SEQ ID NO 13
<211> LENGTH: 19
<212> TYPE: RNA

-continued

```
<213> ORGANISM: Homo sapiens

<400> SEQUENCE: 13
gaagagccag gaaucgaaa                                                   19

<210> SEQ ID NO 14
<211> LENGTH: 19
<212> TYPE: RNA
<213> ORGANISM: Homo sapiens

<400> SEQUENCE: 14
uuucgauucc uggccuucg                                                   19
```

USE OF INHIBITORS OF THE DEGRADATION OF P27, IN PARTICULAR ARGYRIN AND DERIVATIVES THEREOF, FOR THE TREATMENT OF PROLIFERATIVE DISEASES

This application is a National Stage Application of International Application Number PCT/EP2008/001552, filed Feb. 27, 2008; which claims priority to European Application No. 07004185.0, filed Feb. 28, 2007; and claims benefit to U.S. Provisional Application No. 60/965,932, filed Aug. 22, 2007; all of which are incorporated herein by reference in its entirety.

The present invention relates to the use of particular macrocycles that are inhibitors of the proteasomic degradation of p27, in particular Argyrin and derivatives thereof, preferably Argyrin A, for the treatment of proliferative diseases, such as cancer, as well as the derivatization of said macrocycles.

Transitions between phases of the cell cycle are catalyzed by a family of cyclin-dependent kinases (Cdks) (Nurse, 1990; Hartwell, 1991). In some organisms the physiological signals controlling the G2 to M transition target a series of steps that activate the mitotic Cdk, Cdc2. Cdc2 activation is positively regulated by phosphorylation on threonine-161 (Booher and Beach, 1986; Krek and Nigg, 1991; Gould et al., 1991; Solomon et al., 1990; 1992) and negatively by phosphorylation on tyrosine-15 (Gould and Nurse, 1989). Incomplete DNA replication delays dephosphorylation of tyr-15 (Dasso and Newport, 1990; Smythe and Newport, 1992), and mutations in Cdc2 that convert tyr-15 to a nonphosphorylatable residue are lethal and cause a premature mitosis (Gould and Nurse, 1989). Similarly, either over expression of the tyr-15 phosphatase, Cdc25 (Enoch and Nurse, 1990; Kumagai and Dunphy, 1991), or loss of the tyr-15 kinases (Ludgren et al., 1991) bypass the requirement that DNA replication be completed before mitosis begins. Additional levels of control are probably required to fully explain the block to mitosis caused by ongoing DNA replication (Sorger and Murray, 1992; Heald et al., 1993; Stueland et al., 1993). There is also evidence that cell cycle arrest induced by DNA damage may be related to inactivation of Cdc2 (Rowley et al., 1992; Walworth et al., 1993), but the role of tyrosine phosphorylation in this context has been questioned (Barbet and Carr, 1993).

Mammalian cells, like yeast, require cyclin-dependent kinases for progression through G1 and entry into S phase (D'Urso et al., 1990; Blow and Nurse, 1990; Furukawa et al., 1990; Fang and Newport, 1991; Pagano et al., 1993; Tsai et al., 1993). Both D and E-type cyclins are rate limiting for the G1 to S transition and both reduce, but do not eliminate, the cell's requirement for mitogenic growth factors (Ohtsubo and Roberts, 1993; Quelle et al., 1993).

Reduction in the cellular levels of the cyclin kinase inhibitor $p27^{kip1}$ is frequently found in many human cancers and correlate directly with patient prognosis (Philipp-Staheli, J., Payne, S. R. and Kemp, C. J. p27(Kip1): regulation and function of a haplo-insufficient tumour suppressor and its misregulation in cancer. Exp Cell Res 264, 148-68 (2001)). Specifically ubiquitin dependent proteasomal turnover has been shown to cause reduced p27 expression in many human cancers (Loda, M. et al. Increased proteasome-dependent degradation of the cyclin dependent kinase inhibitor p27 in aggressive colorectal carcinomas. Nat Med 3, 231-4 (1997)).

U.S. Pat. No. 5,688,665 describes a protein having an apparent molecular weight of about 27 kD and capable of binding to and inhibiting the activation of a cyclin E-Cdk2 complex, designated as p27. Furthermore, methods of determining whether an agent is capable of specifically inhibiting or enhancing the ability of p27 protein to inhibit the activation of cyclin E-Cdk2 complex are described. Likewise, U.S. Pat. No. 6,355,774 discloses the p27 protein as well as a method for producing p27 in cultured cells. In vitro assays for discovering agents which affect the activity of p27 are also provided. Furthermore, methods of diagnosing and treating hypoproliferative disorders are provided.

Porter et al. (Porter P L, Barlow W E, Yeh I T, Lin M G, Yuan X P, Donato E, Sledge G W, Shapiro C L, Ingle J N, Haskell C M, Albain K S, Roberts J M, Livingston R B, Hayes D F. p27Kip1 and Cyclin E Expression and Breast Cancer Survival After Treatment With Adjuvant Chemotherapy. J Natl Cancer Inst. 2006 Dec. 6; 98(23):1723-31.) describe that abnormal expression of the cell cycle regulatory proteins p27(Kip1) (p27) may be associated with breast cancer survival and relapse. Lower p27 expression was associated with worse overall survival and disease-free survival than higher p27 expression. Low p27 expression appears to be associated with poor prognosis, especially among patients with steroid receptor-positive tumors.

WO 02/055665 in Example 8 thereof describes assays that have been used to identify the interaction of Skp2 and p27 in vitro. The assays are described as useful in order to test for compounds that inhibit cell proliferation. The assays can be carried out in the presence or absence of molecules, compounds, peptides, and said molecules identified by the assays are described potentially useful drugs as therapeutic agents against cancer and proliferative disorders. No specific molecules as identified are described.

Similarly, US 2006-35280 describes rapid screening of large compound libraries using a homogeneous time-resolved fluorescence assay for identification of inhibitors of Cks1-Skp2 binding that plays a critical role in the ubiquitin-dependent degradation of p27.

Pohl et al. (Pohl G, Rudas M, Dietze O, Lax S, Markis E, Pirker R, Zielinski C C, Hausmaninger H, Kubista E, Samonigg H, Jakesz R, Filipits M. High p27Kip1 expression predicts superior relapse-free and overall survival for pre-menopausal women with early-stage breast cancer receiving adjuvant treatment with tamoxifen plus goserelin. J Clin Oncol. 2003 Oct. 1; 21(19):3594-600.) describe that high p27Kip1 expression independently predicted superior relapse-free survival and overall survival in patients treated with combination endocrine therapy. High p27Kip1 expression thus may be useful for the selection of pre-menopausal women with early-stage hormone receptor-positive breast cancer for adjuvant combination endocrine therapy.

GB 2,367,553 discloses pharmaceutically active macrocycles and respective pharmaceutical preparations for the treatment of autoimmune diseases, the induction of immunotolerance or the treatment of bacterial infections.

It is an object of the present invention to provide compounds that can be used and strategies that can be pursued in order to stabilize p27, in order to be used as therapeutic agents for the treatment of proliferative diseases, and in particular cancerous diseases.

According to a first aspect of the present invention, this object is solved by the use of a compound of the general formula I

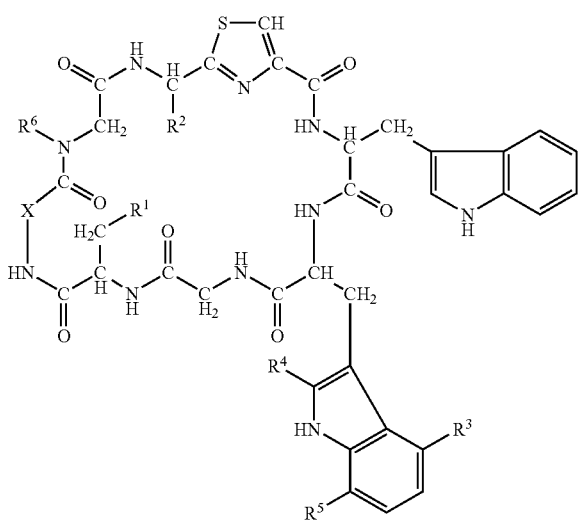

(formula I)

wherein
R¹ and R², are hydrogen, $C_1$-$C_4$ alkyl which is unsubstituted or substituted by OH, or $C_1$-$C_4$ alkoxy;
R³ is hydrogen, $C_1$-$C_8$ alkyl which is unsubstituted or substituted by OH or OR, wherein R is selected from hydrogen, $C_1$-$C_4$ alkyl, aryl or acetyl,
R⁴ is hydrogen, halogen, $C_1$-$C_4$ alkyl which is unsubstituted or substituted by OH, or $C_1$-$C_4$ alkoxy;
R⁵ is hydrogen or halogen;
R⁶ is hydrogen or $C_1$-$C_4$ alkyl; and
X is C=$CH_2$ or $CHR^7$ wherein R⁷ is $C_1$-$C_4$ alkyl which is unsubstituted or substituted by —S—$C_1$-$C_4$ alkyl, and pharmaceutically acceptable salts thereof,
for the production of a medicament for the treatment of cancer in a subject.

Preferred is a use according to the present invention, wherein
R¹, R², and R³ independently are hydrogen, $C_1$-$C_4$ alkyl which is unsubstituted or substituted by OH, or $C_1$-$C_4$ alkoxy;
R⁴ is hydrogen, halogen, $C_1$-$C_4$ alkyl which is unsubstituted or substituted by OH, or $C_1$-$C_4$ alkoxy;
R⁵ is hydrogen or halogen;
R⁶ is hydrogen or $C_1$-$C_4$ alkyl; and
X is C=$CH_2$ or $CHR^7$ wherein R⁷ is $C_1$-$C_4$ alkyl which is unsubstituted or substituted by —S—$C_1$-$C_4$ alkyl, and pharmaceutically acceptable salts thereof,
for the production of a medicament for the treatment of cancer in a subject.

It will be understood that the above defined compounds may bear substituents within their structure, e.g. may bear appropriate amino moiety substituents.

Alkyl groups and moieties in the compounds of formula I may be branched or straight chain. Alkyl groups are suitably straight chain.

Further preferred is a use according to the present invention, wherein
R¹ is hydrogen or unsubstituted $C_1$-$C_4$ alkyl, e.g. methyl;
R² is hydrogen or $C_1$-$C_4$ alkyl which is unsubstituted or substituted by OH, e.g. methyl or hydroxymethyl;
R³ is hydrogen or $C_1$-$C_4$ alkoxy, e.g. methoxy;
R⁴ is hydrogen or unsubstituted $C_1$-$C_4$ alkyl, e.g. methyl;
R⁵ is hydrogen or bromo;
R⁶ is hydrogen or methyl; and
X is C=$CH_2$ or $CHR^7$ wherein R⁷ is methyl which is unsubstituted or substituted by —S-ethyl,
and pharmaceutically acceptable salts thereof.

Even further preferred is a use according to the present invention, wherein
R¹ is hydrogen or methyl;
R² is methyl or hydroxymethyl;
R³ is hydrogen or methoxy;
R⁴ is hydrogen or methyl;
R⁵ is hydrogen;
R⁶ is methyl; and
X is C=$CH_2$,
and pharmaceutically acceptable salts thereof.

Preferred is a method according to the present invention comprising providing argyrin A and pharmaceutically acceptable salts thereof to a patient in need thereof. Further particularly preferred are argyrin B

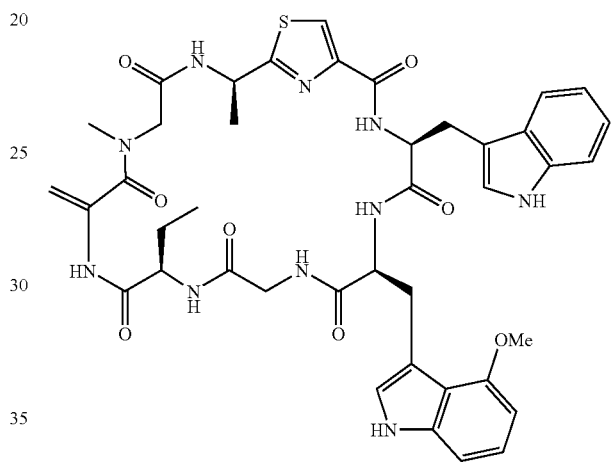

or, in particular, argyrin F, and pharmaceutically acceptable salts thereof.

For argyrins, the following definitions apply (R⁵ is H, and R⁶ is Me)

| Argyrin | R¹ | R² | R³ | R⁴ |
|---|---|---|---|---|
| A | H | $CH_3$ | $OCH_3$ | H |
| B | $CH_3$ | $CH_3$ | $OCH_3$ | H |
| C | H | $CH_3$ | $OCH_3$ | $CH_3$ |
| D | $CH_3$ | $CH_3$ | $OCH_3$ | $CH_3$ |
| E | H | $CH_3$ | H | H |
| F | H | $CH_2OH$ | $OCH_3$ | H |
| G | $CH_3$ | $CH_2OH$ | $OCH_3$ | H |
| H | H | H | $OCH_3$ | H |

Preferred is a method according to the present invention, wherein the subject is a mammal, in particular a human.

Sasse F et al. (in Sasse F, Steinmetz H, Schupp T, Petersen F, Memmert K, Hofmann H, Heusser C, Brinkmann V, von Matt P, Hofle G, Reichenbach H. Argyrins, immunosuppressive cyclic peptides from myxobacteria. I. Production, isolation, physico-chemical and biological properties. J Antibiot (Tokyo). 2002 June; 55(6):543-51.) describe the production of a group of cyclic peptides called argyrins, as well as some of their biological properties. Cancer is not mentioned. Vollbrecht et al. (in Vollbrecht L, Steinmetz H, Hofle G, Oberer, L, Rihs G, Bovermann G, and von Matt P. Argyrins, immunosuppressive cyclic peptides from myxobacteria. II. Structure elucidation and stereochemistry. J Antibiot (Tokyo). 2002 August; 55(8):715-721.) describe the structure of said cyclic peptides.

Similarly, Ley et al. (in Ley S V, Priour A, Heusser C. Total synthesis of the cyclic heptapeptide Argyrin B: a new potent inhibitor of T-cell independent antibody formation. Org. Lett. 2002 Mar. 7; 4(5):711-4.) describe the synthesis of argyrin B and its function as inhibitor of antibody formation. Cancer is also not mentioned.

More preferred is a method according to the present invention, wherein the treatment of the proliferative disorders and/or cancer comprises blocking tumor cell growth, blocking and/or destroying the existing tumour vasculature, treatment of breast cancer, treatment of hepatocellular carcinoma, treatment of cervix carcinoma, treatment of lung carcinoma, treatment of multiple myeloma, and/or treatment of colon cancer, and treatment of psoriasis.

Another aspect of the present invention then relates to a use according to the present invention, wherein the medicament further comprises additional pharmaceutically active antitumor ingredients, such as paclitaxel.

Preliminary mouse experiments as performed by the present inventors show that Argyrin is active already at a concentration of 0.03 mg/kg body weight. Another aspect of the present invention thus relates to a use according to the present invention, wherein the compound, such as, for example, Argyrin A or F, is administered at a dose of 0.01 mg to 200 mg/kg, preferably at a dose of 0.01 mg to 100 mg/kg, most preferably at a dose of 0.02 mg to 10 mg/kg, optimally given per day. Another example is 0.15 mg Argyrin per kilogram bodyweight injected intraperitoneally every three days.

In certain embodiments of the invention, the administration can be designed so as to result in sequential exposures to the compound over some time period, e.g., hours, days, weeks, months or years. This can be accomplished by repeated administrations of the compound, e.g., by one of the methods described above, or alternatively, by a controlled release delivery system in which the compound is delivered to the subject over a prolonged period without repeated administrations. By a controlled release delivery system is meant that total release of the compound does not occur immediately upon administration, but rather is delayed for some time. Release can occur in bursts or it can occur gradually and continuously. Administration of such a system can be, e.g., by long acting oral dosage forms, bolus injections, transdermal patches or subcutaneous implants. Examples of systems in which release occurs in bursts include, e.g., systems in which the compound is entrapped in liposomes which are encapsulated in a polymer matrix, the liposomes being sensitive to a specific stimulus, e.g., temperature, pH, light, magnetic field, or a degrading enzyme, and systems in which the compound is encapsulated by an ionically-coated microcapsule with a microcapsule core-degrading enzyme. Examples of systems in which release of the compound is gradual and continuous include, e.g., erosional systems in which the compound is contained in a form within a matrix, and diffusional systems in which the compound permeates at a controlled rate, e.g., through a polymer. Such sustained release systems can be, e.g., in the form of pellets or capsules.

The compound can be administered prior to or subsequent to the appearance of disease symptoms. In certain embodiments, the compound is administered to patients with familial histories of the disease, or who have phenotypes that may indicate a predisposition to the disease, for example breast cancer, or who have been diagnosed as having a genotype which predisposes the patient to the disease, or who have other risk factors.

The compound according to the invention is administered to the subject in a therapeutically effective amount. By therapeutically effective amount is meant that amount which is capable of at least partially preventing or reversing the disease. A therapeutically effective amount can be determined on an individual basis and will be based, at least in part, on consideration of the species of subject, the subject's size, the subject's age, the efficacy of the particular compound used, the longevity of the particular compound used, the type of delivery system used, the time of administration relative to the onset of disease symptoms, and whether a single, multiple, or controlled release dose regimen is employed. A therapeutically effective amount can be determined by one of ordinary skill in the art employing such factors and using no more than routine experimentation.

In certain preferred embodiments, the concentration of the compound is at a dose of about 0.1 to about 1000 mg/kg body weight/day, more preferably at about 0.01 mg to 200 mg/kg, preferably at a dose of about 0.01 mg to 100 mg/kg, most preferably at a dose of 0.02 mg to 10 mg/kg. Preferably, the dosage form is such that it does not substantially deleteriously affect the subject.

Compounds of the invention may also be administered systemically or topically, by any conventional route, in particular enterally, e.g. orally, e.g. in the form of tablets or capsules, parenterally, e.g. in the form of injectable solutions or suspensions, topically, e.g. in the form of lotions, gels, ointments or creams, or in nasal or a suppository form.

Compounds of formula I an derivatives thereof may be prepared synthetically by methods known to the skilled person in the art of peptide chemistry, e.g. by a process comprising ring formation of a suitable oligopeptide, or, alternatively, may be isolated from the culture broth of a suitable microorganism. Preparation may include an additional modification step, e.g. hydration of an exocyclic double bond, an addition reaction step or a halogenation step. A suitable microorganism may be identified by culturing a variety of different microorganisms, e.g. selected from the group of myxobacteria and screening the resulting culture broths for the presence of a compound of formula I, in particular for a compound of formula I wherein $R^1$, $R^2$, $R^3$, and $R^4$ independently are hydrogen, $C_1$-$C_4$ alkyl which is unsubstituted or substituted by OH, or $C_1$-$C_4$alkoxy; $R^5$ is hydrogen; and X is C=$CH_2$.

Isolation may follow methods commonly known to the skilled person. A suitable approach may, e.g., comprise culturing the microorganisms in the presence of a solid phase, e.g. a resin, e.g. amberlite, adsorbing the compound of formula I, and eluting the compound of formula I from the solid phase.

Another aspect of the present invention then relates to a method for screening a compound for the ability to inhibit the degradation of p27, comprising contacting a cell with a compound suspected to inhibit the degradation of p27, assaying the contents of the cell to determine the amount and/or biological activity of p27 and/or the cell cycle status, and comparing the determined amount and/or biological activity of p27 or the cell cycle status with the amount and/or biological activity of p27 or the cell cycle status as found without the compound, wherein a change of said amount and/or biological activity of p27 or the cell cycle status is indicative for a compound that inhibits the degradation of p27.

Methods of assaying the contents of the cell that is contacted with the compound to be screened, in order to determine the amount and/or biological activity of p27 and/or the cell cycle status are well known to the person of skill and include Western blots for p27, expression analysis of p27 (e.g. by means of rtPCR), and analysis of a fusion protein, such as, for example, p27-GFP (green fluorescent protein), as well as the analysis of cell cycle markers. Preferred is a method according to the present invention, wherein the amount of p27 GFP is determined.

Preferred is a method according to the present invention, wherein the screened compound influences the proteasomic degradation of p27 as determined by the amount of a fusion protein, such as p27-GFP.

Preferred is a method according to the present invention, wherein the investigated assay cell is a tumour cell or cell line, such as a breast cancer cell line, a hepatocellular carcinoma cell line, a cervix carcinoma cell line, a lung carcinoma cell line, and/or a colon cancer cell line.

More preferred is a method according to the present invention, wherein the method further comprises a chemical modification of the compound as identified. In this case, the compound as screened will function as a so-called "lead-structure" which is further subjected to chemical modifications which are then screened for their effectiveness to increase the amount and/or biological activity of p27 in one or more subsequent screening methods as above.

Modification can be effected by a variety of methods known in the art, which include without limitation the introduction of novel side chains or the exchange of functional groups like, for example, introduction of halogens, in particular F, Cl or Br, the introduction of lower alkyl groups, preferably having one to five carbon atoms like, for example, methyl, ethyl, n-propyl, isopropyl, n-butyl, isobutyl, tert-butyl, n-pentyl or iso-pentyl groups, lower alkenyl groups, preferably having two to five carbon atoms, lower alkinyl groups, preferably having two to five carbon atoms or through the introduction of, for example, a group selected from the group consisting of $NH_2$, $NO_2$, OH, SH, NH, CN, aryl, heteroaryl, COH or COOH group. Furthermore, additional peptide groups could be added to the molecule, such as single amino acids, dipeptides, tripeptides, and so on.

If needed the steps of selecting the compound, modifying the compound, and measuring the effect of the modified compounds to the protein can be repeated a third or any given number of times as required. The above described method is also termed "directed evolution" since it involves a multitude of steps including modification and selection, whereby effective compounds are selected in an "evolutionary" process optimizing its capabilities with respect to a particular property, i.e. to stabilize p27.

Preferred is a method according to the present invention, wherein a compound according to formula I as above, wherein R1, R2 and R3 independently are hydrogen, $C_1$-$C_4$ alkyl which is unsubstituted or substituted by OH, or $C_1$-$C_4$ alkoxy; R4 is hydrogen, halogen, $C_1$-$C_4$ alkyl which is unsubstituted or substituted by OH, or $C_1$-$C_4$ alkoxy; R5 is hydrogen or halogen; R6 is hydrogen or $C_1$-$C_4$ alkyl; and X is C=CH2 or CHR6 wherein R6 is $C_1$-$C_4$ alkyl which is unsubstituted or substituted by —S—$C_1$-$C_4$ alkyl, and pharmaceutically acceptable salts thereof, is chemically modified, that is, is used as a lead structure for "directed evolution".

Yet another aspect of the present invention is directed to a method for producing a pharmaceutical composition, comprising (a) screening method(s) according to the present invention, and formulating the screened compound with pharmaceutically acceptable carriers and/or excipients. Carriers, excipients and strategies to formulate a pharmaceutical composition, for example to be administered systemically or topically, by any conventional route, in particular enterally, e.g. orally, e.g. in the form of tablets or capsules, parenterally, e.g. in the form of injectable solutions or suspensions, topically, e.g. in the form of lotions, gels, ointments or creams, or in nasal or a suppository form are well known to the person of skill and described in the respective literature.

Administration of an agent, e.g., a compound can be accomplished by any method which allows the agent to reach the target cells. These methods include, e.g., injection, deposition, implantation, suppositories, oral ingestion, inhalation, topical administration, or any other method of administration where access to the target cells by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed. The agent can be suspended in liquid, e.g., in dissolved or colloidal form. The liquid can be a solvent, partial solvent or non-solvent. In many cases, water or an organic liquid can be used.

Yet another aspect of the present invention is directed to a pharmaceutical composition that is produced according to the method as above.

Another aspect of the present invention relates to a method of treating cancer in a subject, comprising administering an effective amount of the pharmaceutical preparation according to present invention to a subject in need of said treatment. Preferably, said cancer is selected from breast cancer, hepatocellular carcinoma, cervix carcinoma, lung carcinoma, and colon cancer or proliferative disorders as above. Preferably, said patient is a human being. Treating is meant to include, e.g., preventing, treating, reducing the symptoms of, or curing the disease or condition.

The invention also includes a method for treating a subject at risk for a disease as above, wherein a therapeutically effective amount of a compound as above is provided. Being at risk for the disease can result from, e.g., a family history of the disease, a genotype which predisposes to the disease, or phenotypic symptoms which predispose to the disease.

Another aspect of the present invention relates to a use as above, wherein the medicament further comprises additional pharmaceutically active ingredients that modulate cancer, such as breast cancer, hepatocellular carcinoma, cervix carcinoma, lung carcinoma, and colon cancer or agents that modulate other proliferative diseases, such as anti-psoriasis agents.

The inventors recently demonstrated that expression of a stabilized version of $p27^{kip1}$ ($p27^{kip1}$T187A) in a genetically modified mouse significantly reduced the number of intestinal adenomatous polyps which progressed to invasive carcinomas (Timmerbeul, I. et al. Testing the importance of p27 degradation by the SCFskp2 pathway in murine models of lung and colon cancer. *Proc Natl Acad Sci USA* 103, 14009-14 (2006)). Based on this work, the inventors set out to identify compounds which lead to a re-expression of p27 in cancer tissues. In this work the inventors identify Argyrin A, a compound derived from myxobacterium *archangium gephyra*, as a potent inducer of p27kip1 expression. Argyrin A induces apoptosis in human cancer cell lines and tumour xenografts in vivo. Importantly, by inducing $p27^{kip1}$ it also targets the existing tumour vasculature which leads to destruction of tumour tissue in vivo. Argyrin A functions are strictly dependent on the expression of $p27^{kip1}$ as neither tumour cells nor endothelial cells which do not express $p27^{kip1}$ respond to this compound. Surprisingly, the molecular mechanism by which Argyrin A exerts its p27 dependent biological function is through a potent inhibition of the 20S proteasome.

To identify substances which lead to an increase in the expression levels of p27$^{kip1}$ the inventors generated a cell based high throughput assay system (see materials and methods for details). One of the substances which exerted the strongest increase in fluorescence was identified as Argyrin A, a cyclical peptide which had originally been identified as a metabolic product derived from myxobacterium *archangium gephyra* (Sasse, F. et al. Argyrins, immunosuppressive cyclic peptides from myxobacteria. I. Production, isolation, physicochemical and biological properties. *J Antibiot (Tokyo)* 55, 543-51 (2002) FIG. 5A). As shown by flow cytometry, Argyrin A exerted two different cellular phenotypes at ranges of IC$_{50}$. While primary human fibroblasts, A549 (lung cancer) and HCT116 colon carcinoma cells stopped to proliferate, colon carcinoma cell lines SW480, CaCo as well as MCF7 (breast cancer) and HeLa (cervix carcinoma) cells underwent apoptosis as shown by a dramatic increase in the sub G1 phase fraction. The apoptosis inducing activity of Argyrin A was confirmed by measuring DNA fragmentation using a histone fragmentation ELISA (FIG. 5B).

The time course experiment displayed in FIG. 1B shows that Argyrin A induced an increase in cellular p27$^{kip1}$ levels in SW480 and HCT116 colon carcinoma, and HeLA cells. To determine whether the Argyrin A induced change in p27$^{kip1}$ expression levels was due to an increase in its stability the inventors measured the half life of p27$^{kip1}$ in HeLa and SW480 cells in the presence and absence of Argyrin A. FIG. 1C shows a quantification of the expression levels of p27$^{kip1}$ compared to actin in cycloheximide treated cells which were incubated with Argyrin A or left untreated. Argyrin A treatment results in a complete block in p27 turnover in these cells. As all known p27 turnover mechanisms involve proteolytic destruction of the protein by the 20S proteasome, the inventors next measured the activity of purified human proteasomes after incubation with increasing amounts of Argyrin A. FIG. 1D shows that incubation of purified human 20S proteasome with Argyrin A led to a dose dependent inhibition of the caspase, trypsin and chymotrypsin like proteasome activities. Importantly the extent of proteasome inhibition by Argyrin A was comparable to what was measured with the clinically used proteasome inhibitor bortezomib (Velcade) in vitro. In line with the ability of Argyrin A to inhibit the proteasome the inventors found that other well known proteasome substrates namely p53, p21, BAX and NfkB also accumulated in response to Argyrin A treatment (FIG. 1E). The inventors therefore conclude that Argyrin A prevents the degradation of p27 due to its proteasome inhibitory activity in vivo and induces apoptosis or G1 arrest in a variety of different tumour cell lines.

Next the inventors tested whether the stabilization of p27 was indeed required for the apoptosis inducing function of Argyrin A or was merely a consequence of proteasome inhibition. For this the inventors treated immortalized mouse embryonic fibroblasts from p27$^{kip1}$ wildtype or knockout mice with Argyrin A or the proteasome inhibitor bortezomib and assayed cell cycle distribution and apoptosis by flow cytometry. Bortezomib treatment induced apoptosis after 24 hours in both cell lines irrespective of p27$^{kip1}$ status. FIG. 2A shows a quantification of the sub G1 fractions in p27 wildtype and knockout MEFs (see also FIG. 6A). The same response was observed with MG132 treatment. In strong contrast Argyrin A treatment induced apoptosis only in cells which expressed p27$^{kip1}$ while only ten percent of p27$^{kip1}$ knockout fibroblasts underwent apoptotic cell death after 60 hours of treatment. These differences in sensitivity in response to Argyrin A treatment were not due to differences in the accumulation of other proteasomal substrates in p27 wildtype and knockout cells as p53 and p21 levels increased in both cell lines in response to Argyrin A (FIG. 6B). To extend this observation to human cancer cells the inventors reduced the levels of p27$^{kip1}$ in HeLa cells using p27$^{kip1}$ specific siRNA. As shown in FIG. 2F HeLa cells which express p27$^{kip1}$ underwent apoptosis in response to Argyrin A while treatment with p27siRNA completely blocked the apoptosis inducing function of this compound.

The inventors' analysis shows that while both proteasome inhibitors Argyrin A and bortezomib, are able to block proteasome activity in vitro only Argyrin A requires p27$^{kip1}$ expression to induce cell death. The inventors therefore decided to directly test the extent to which the cellular effects of proteasome inhibition per se are influenced by p27$^{kip1}$ expression. For this the inventors designed specific siRNA molecules which target the β1 (caspase-like activity), β2 (trypsin-like activity) and β5 (chymotrypsin-like activity) subunits of the mouse 20S-proteasome. The inventors then reduced the expression of these subunits in embryonic fibroblasts derived from wildtype or p27$^{kip1}$ knockout cells and measured proteasome activity and cell cycle distribution. FIGS. 2B and 2D show activity measurements for the caspase, chymotrypisn and trypsin-like activities of the proteasome after treatment with Argyrin A or a combination of siRNAs against the β1, β2 and β5 subunits. The levels of proteasome subunit expression are displayed in the corresponding western blots. The degree of inhibition the inventors reached with siRNA mediated knockdown of proteasomal subunits was comparable to the effects exerted by Argyrin A or bortezomib treatment in vivo (FIG. 3A). The levels of proteasome subunit expression are displayed in the corresponding western blots.

Loss of proteasome activity in wildtype fibroblasts led to the induction of apoptosis in 38% (Argyrin A) or 45% (siRNA) of all cells after 24 hours (FIG. 2C). Importantly only 5% (Argyrin A) or 6% (siRNA) of all fibroblasts derived from p27 knockout mice underwent apoptosis at comparable levels of proteasome inhibition (FIG. 2E) while treatment of p27 wildtype or knockout cells with bortezomib induced massive apoptosis independent of the p27 status (FIG. 2A). These results point towards an as yet unrecognized role of p27$^{kip1}$ as a critical regulator of apoptotic cell death in response to proteasome inhibition.

The inventors decided to compare the cellular responses of cells treated with Argyrin A or bortezomib directly. To this end the inventors determined the gene expression signature of MCF7 cells in response to Argyrin A or bortezomib and compared the resulting gene expression profiles. FIG. 6C shows a correlation plot of the gene expression data which the inventors obtained in these experiments using untreated, Argyrin A or bortezomib treated MCF7 cells. FIG. 6D shows the correlation values. As shown in FIG. 2G the gene expression profiles of MCF7 cells which were treated with either bortezomib or Argyrin A differ dramatically. While bortezomib treatment led to changes in the expression of more than 10900 genes, only about 500 genes changed in response to Argyrin A treatment. Among these genes, 311 were affected by both bortezomib and Argyrin A, respectively. The functional gene clustering based on their corresponding gene ontology terms indicates that while Argyrin A and bortezomib both inhibit the 20S proteasome they cause very divergent pertubations on the cellular level. From this data the inventors conclude that Bortezomib treatment affects additional targets in the cell which result in the activation of various cellular responses thereby making bortezomib induced cell death independent of $p27^{kip1}$ expression.

The inventors recently demonstrated that $p27^{kip1}$ stabilization prevents the progression from adenomatous polyps to invasive intestinal cancers. The inventors therefore tested if Argyrin A induced $p27^{kip1}$ stabilization would be beneficial in the treatment of human colon cancer cell derived tumour xenografts. To analyze this the inventors first tested if Argyrin A was active after application in vivo. After intraperitoneal injection of Argyrin A, 20S proteasome was isolated from peripheral blood lymphocytes at different time points after injection. As shown in FIG. 3A Argyrin A inhibited all proteasome activities after i.p. application. The maximum inhibitory activity was reached at 48 h post injection and all activities returned to base-line levels at 72 hours post injection. Based on this finding the inventors treated tumour bearing mice with 0.15 mg Argyrin per kilogram bodyweight injected intraperitoneally every three days.

As shown in FIG. 3B Argyrin A led to significant reduction in the size of the xenotrans-planted tumours used in these experiments. The extent and kinetics of tumour regression were comparable or even more pronounced to what was observed in the bortezomib treated animals. Importantly however the inventors did not observe any signs of discomfort, weight loss (FIG. 3C) or disease in the Argyrin A compared to the bortezomib treated animals.

To assay the extent of proteasome inhibition, the induction of $p27^{kip1}$ and the development of apoptotic cell death in primary tumour tissue the inventors treated tumour bearing mice with a single dose of Argyrin A or bortezomib and explanted tumours at the indicated time points thereafter. As shown in FIG. 3D, both, bortezomib and Argyrin A treatments, led to a significant reduction of proteasome activity in the primary tumour tissue.

Importantly Argyrin A treatment resulted in an induction of $p27^{kip1}$ and apoptotic cell death in more then 60% of all tumor cells (FIG. 3 E, F). This result was not unexpected as SW480 cells were highly sensitive to Argyrin A treatment in vitro. The inventors therefore decided to test whether Argyrin A would also show an effect against HCT116 derived tumor-xenografts as these cell lines did not undergo apoptosis in vitro but instead arrested in the G1 phase. The result of these experiments are shown in FIG. 4A. While the reduction in tumour size was not as pronounced as in SW480 derived xenotransplants the inventors still observed a significant reduction in tumour volume after treatment with Argyrin A. Interestingly when SW480 or HCT116 derived tumours were explanted they uniformly showed a large necrotic area in the centre of the tumour which was filled with blood and necrotic tumour tissue (FIG. 4B). This phenotype is often observed with drugs which interfere with blood vessel formation or compounds which directly damage existing tumour vessels. The inventors therefore determined the microvessel density in tumour tissues (SW480 or HCT116) from mice which received a single injection of Argyrin A. FIG. 4C shows that Argyrin A leads to a significant reduction in the number of CD31 positive endothelial cells starting as early as 90 minutes after injection with only about 10% of CD31 positive cells remaining at 72 hours after injection (see supplemental FIG. 3A for a representative staining). This reduction in tumour vasculature was paralleled by an induction of $p27^{kip1}$ expression in the CD31 positive endothelial cells. (FIG. 7A). To understand this phenotype in more detail the inventors analyzed primary tumour material by electronic microscopy. As early as 90 minutes after injection the inventors observed swelling of endothelial cell which was followed by a loss of basal membrane attachment and cell-cell contacts (FIG. 4D) in the tumour vasculature. As a result of the apparent loss of cell and basal membrane attachment after Argyrin A treatment many of the examined tumour blood vessels were occluded with endothelial cells or erythrocytes. The destruction of the tumour core which the inventors observed after Argyrin A treatment might therefore be a result of thrombotic occlusion of the affected blood vessels. In contrast the bortezomib induced reduction in CD31 positive cells correlated with the appearance of necrotic endothelial cells (FIG. 4D).

The inventors then asked whether Argyrin A was also able to prevent the formation of capillary like tube structures formed by HUVEC on matrigel, an assay frequently used to test the ability of a compound to interfere with neovascularization. FIG. 4E shows a quantification of the relative length of capillary tubes formed by HUVEC upon stimulation with VEGF. The addition of Argyrin A led to a 40% reduction in tube formation in this assay. Importantly transfection of siRNA against p27 protected endothelial cells against the inhibitory activity of Argyrin A. The effects exerted by Bortezomib in this assay were smaller and not rescued by loss of p27. In addition to tube length the inventors also quantitated the number of blood vessel like structures formed by HUVECS after treatment with Argyrin A or bortezomib (FIG. 4F). Both treatments led to a significant reduction in vessel like structures. However loss of p27 only had a significant effect on the Arygrin A induced phenotype, reinforcing the conclusion that Argyrin A exerts its biological functions through an increase in $p27^{kip1}$ expression.

In this work the inventors identify the myxobacterium derived cyclical peptide Argyrin A as a compound which exerts its biological functions by blocking the cellular turnover of $p27^{kip1}$. Stabilization of $p27^{kip1}$ led to either G1 arrest or apoptosis in different human tumour cells in vitro. By treating xenotransplant tumours derived from human colon cancer cell lines the inventors furthermore show that Argyrin A also affects the tumour vasculature. Its anti-angiogenic activities encompass the inhibition of neo-vascularization in vitro but even more pronounced the destruction of established tumour blood vessels in vivo. The inventors show that the destruction of the tumour core is accompanied by a detachment of endothelial cells from the basal membrane and by a loss of cell-cell contacts. Similarly HUVEC cells in vitro show a reduction in the formation of local adhesions and stress fibres after treatment with Argyrin A which correlates with reduced RhoA activity. In the same context loss or suppression of $p27^{kip1}$ expression in tumour cells conferred resistance to the apoptosis inducing activity of Argyrin A. Together these observations support the conclusion that Argyrin A anti-tumour activities are mediated through the stabilization of $p27^{kip1}$.

The molecular mechanism by which Argyrin A stabilizes $p27^{kip1}$ is through the inhibition of the 20S proteasome. This conclusion is based on the observation that Argyrin A is able to inhibit all proteasomal activities of purified 20S proteasome in vitro a well as in peripheral blood cells and in tumour tissues in vivo. By blocking proteasome activity with siRNA directed against critical subunits the inventors surprisingly find that $p27^{kip1}$ is indeed required for the apoptosis inducing function of proteasome inhibition per se. Loss or reduced expression of $p27^{kip1}$ might therefore result in an increased resistance of tumour cells against processes which lead to the accumulation of proteins which are normally degraded by the proteasome. The inventors suggest that $p27^{kip1}$ stabilization through Argyrin A, and other Argyrins as described herein, such as in particular Argyrin F, represents a valuable new strategy for the treatment of human malignancies.

Another aspect of the present invention then relates to a method according to the present invention, wherein the medicament further comprises additional pharmaceutically active anti-tumor ingredients, such as paclitaxel and/or bortezomib.

Another aspect of the present invention relates to a method of treating cancer in a subject, comprising administering an effective amount of the pharmaceutical preparation according to present invention to a subject in need of said treatment. Preferably, said cancer is selected from breast cancer, hepatocellular carcinoma, cervix carcinoma, lung carcinoma, and colon cancer. Preferably, said patient is a human being. Treating is meant to include, e.g., preventing, treating, reducing the symptoms of, or curing the disease or condition.

The invention also includes a method for treating a subject at risk for a disease as above, wherein a therapeutically effective amount of a compound as above is provided. Being at risk for the disease can result from, e.g., a family history of the disease, a genotype which predisposes to the disease, or phenotypic symptoms which predispose to the disease.

The following figures, sequences, and examples merely serve to illustrate the invention and should not be construed to restrict the scope of the invention to the particular embodiments of the invention described in the examples. For the purposes of the present invention, all references as cited herein are hereby incorporated herein by reference in their entireties.

SEQ ID Nos. 1 to 14 show the sequences of siRNA molecules as used in the present invention.

LEGENDS FOR FIGURES

FIG. 1 shows that argyrin A induces p27 stabilization through inhibition of the 20S proteasome. a) The indicated cell lines were treated with Argyrin A and the G1 and sub-G1 fractions were determined by flow cytometric analysis of propidium iodide stained cells. IC50 values were determined by MTT cell proliferation assays using different concentrations of Argyrin A. The IC50 value was calculated as the half-maximal concentration at which Argyrin A exerted an effect. b) SW480, HCT116 and HeLa cells were treated with Argyrin A after which cells were lysed at the indicated timepoints to determine the expression levels of $p27^{kip1}$ by western blotting. c) SW480 and HeLa cells were treated with Argyrin A or left untreated for 12 hours after which time cycloheximide was added at a concentration of 25 μg/mL. The expression levels of $p27^{kip1}$ were determined at the indicated timepoints by western blotting and normalized against actin expression which was used as an internal control. The graphs shows a quantification of three independent experiments. d) Purified human erythrocyte derived 20S proteasome was incubated with the indicated amounts of Argyrin A or bortezomib and the activity of the caspase-, chymotrypsin- and trypsin-like proteasome activities were measured using fluorogenic peptide substrates specific for the different catalytic activities. e) SW480 and HCT116 cell lines were incubated with Argyrin A. At the indicated timepoints cells were lysed and the expression levels of p53, p21, Bax, NfkB and actin were analysed by western blotting.

FIG. 2 shows that apoptosis induced by proteasome inhibition depends on the expression of $p27^{kip1}$ a) To determine if the induction of apoptotic cell death by Argyrin A depends on the expression of $p27^{kip1}$, mouse embryonic fibroblasts (MEF) derived from either wildtype (WT) or p27 knockout mice (KO) were treated with Argyrin A. The number of apoptotic cells was determined by measuring the sub-G1 fraction by flow cytometry using propidium iodide stained cells. The results shown are the average numbers for six independent experiments. b+d) Wildtype (b) and p27 knockout (d) MEF were treated with Argyrin A or transfected with siRNAs specific for the β1, β2 or β5 subunit of the proteasome for 24 hours. The graphs show the remaining catalytic activity of the different proteasome subunits after Argyrin A or siRNA treatment compared to an untreated control (n=3). The western blots show the expression of the β1, β2 or β5 subunit of the proteasome in proliferating cells and after treatment with siRNAs for a representative experiment. c+e) Flow cytometric measurements of the number of apoptotic cells (sub-G1 fraction) after Argyrin A or siRNA treatment in wildtype (c) or p27 knockout (E) MEF. f) HeLa cells were treated with Argyrin A or siRNA against p27 or Argyrin A and siRNA against p27 for either 24 or 48 hours. The western blots show the expression levels for p27 in response to the different treatments. g) The heatmap displays a correlation analysis of genome wide gene expression profiles of MCF7 breast cancer cells which were treated with Argyrin A or bortezomib for the indicated times. The corresponding correlation value matrix is given in FIG. 6d.

FIG. 3 shows that argyrin A induces apoptosis in human colon cancer xenografts in vivo a) Mice were i.p. injected with Argyrin A (0.03 mg/kg bodyweight) or bortezomib (1 mg/kg bodyweight). At the indicated timepoints 20S proteasome was isolated from peripheral blood cells and the activity of the different proteasome subunits was determined as described (FIG. 1d). b) SW480 colon carcinoma cell lines mixed with matrigel were injected under the skin of nu/nu mice to establish xenotransplant tumours. Treatment with Argyrin A or bortezomib was started when these tumours reached a volume of 200 mm³. The graph shows a quantification of tumour volumes at the indictated timepoints compared to the starting size which was set as 100 (n=8 Argyrin A (0.15 mg/kg bodyweight), n=4 Bortezomib (0.6 mg/kg bodyweight), n=10 PBS/EtOH control c) All mice were weighed throughout the course of the experiment. The graph shows the changes in body weight for mice treated with Argyrin A or bortezomib. d) Determination of proteasome activity in tumour tissue after treatment with bortezomib and Argyrin A. After a one time injection of the respective compounds tumours were explanted at the indicated time points and proteasomes were extracted from the tumour tissue. The activity of the respective proteasome subunits was determined as described previously (FIG. 1d). e) Determination of the number of $p27^{kip1}$ positive cells in tumour tissue after Argyrin A treatment. The pictures show representative samples of immunohistochemical stainings for p27 in tumour tissues after 10 days of Argyrin A treatment. f) Detection of apoptotic cells in xenotransplanted tumours by TUNEL staining of tumour tissues after treatment with Argyrin A or bortezomib. At least 200 cells were counted on five independent sections to quantitate the number of apoptotic cells.

FIG. 4 shows that argyrin A damages existing tumour blood vessels and interferes with neovascularisation in a $p27^{kip1}$ dependent way. a) HCT116 colon carcinoma cell lines mixed with matrigel were injected under the skin of nu/nu mice to establish xenotransplant tumours. Treatment with Argyrin A or bortezomib was started when these tumours reached a volume of 200 mm3. The graph shows a quantification of tumour volumes at the indicated time points compared to the starting size which was set as 100. (n=8 Argyrin A, n=8 Bortezomib, n=6 PBS/EtOH) b) The pictures show the macroscopic appearance of a xenotransplant tumour after 10 days of treatment with Argyrin A. Note the large necrotic centre of the explanted tumour. c) After a single injection of Argyrin A (0.15 mg/kg bodyweight) or bortezomib (1.0 mg/kg bodyweight) tumours were explanted at the indicated time points and blood vessels in the tumour tissue were co-stained for CD31 and p27. (See also FIG. 7A for representative immunofluorescent stainings) The graph shows a quantification of the data. d) The ultrastructure of microvessels was analysed after injection of Argyrin A (right and middle photographs) or Bortezomib (left photograph), respectively. Note the swelling of the endothelial cell ("E") and the occlusion of the lumen ("L") by erythrocytes after 90 minutes of Argyrin A treatment. The arrow marks the detachment of endothelial cells after 48 h of Argyrin A treatment. The left panel shows apoptotic endothelial cells after treatment with Bortezomib e+f) HUVEC cells were grown in endothel-cell basal medium supplemented with growth factors and containing 2% FCS for 24 h and treated with Argyrin A (1 µM), bortezomib (10 nM), siRNA against p27, Argyrin A and siRNA or bortezomib and siRNA. Tube length (f) and blood vessel like 23 structures were determined using photographs of HUVEC cultures. The micrographs show representative examples of HUVEC cultures under the indicated conditions.

FIG. 5 shows a) the chemical structure of Argyrin A b) The graph shows a quantification of the percentage of apoptotic SW 480 cells as determined by a histone-associated-DNA-fragments ELISA after treatment with Argyrin A. Camptothecin treated U937 cells were used as positive control.

FIG. 6 a) The graphs show representative examples of flow cytometric measurements of wildtype and p27 knockout cells after treatment with Argyrin A or Bortezomib. b) p27 wildtype or knockout MEFs were incubated with Argyrin A and the expression levels of p21, p53, Bax and actin were determined at the indicated timepoints. c) MCF7 breast cancer cells were incubated with Argyrin A or Bortezomib for 24 h or left untreated and the activity of the caspase-, chymotrysin- and trypsin like proteasome activities were measured using fluorogenic peptide substrates specific for the different catalytic activities. d) Correlation values for FIG. 2G.

MATERIALS AND METHODS

Figure 1:
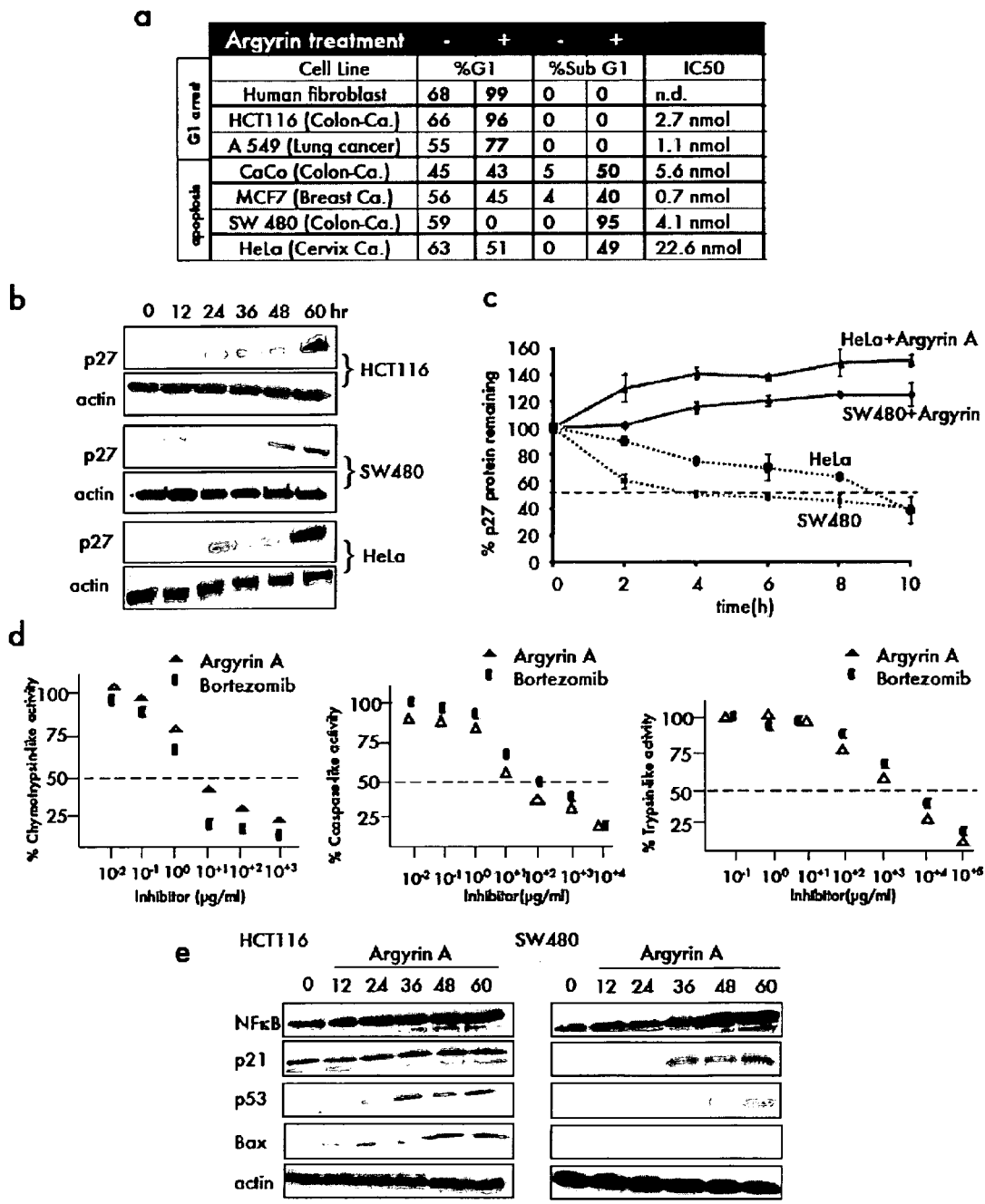
Figure 2:
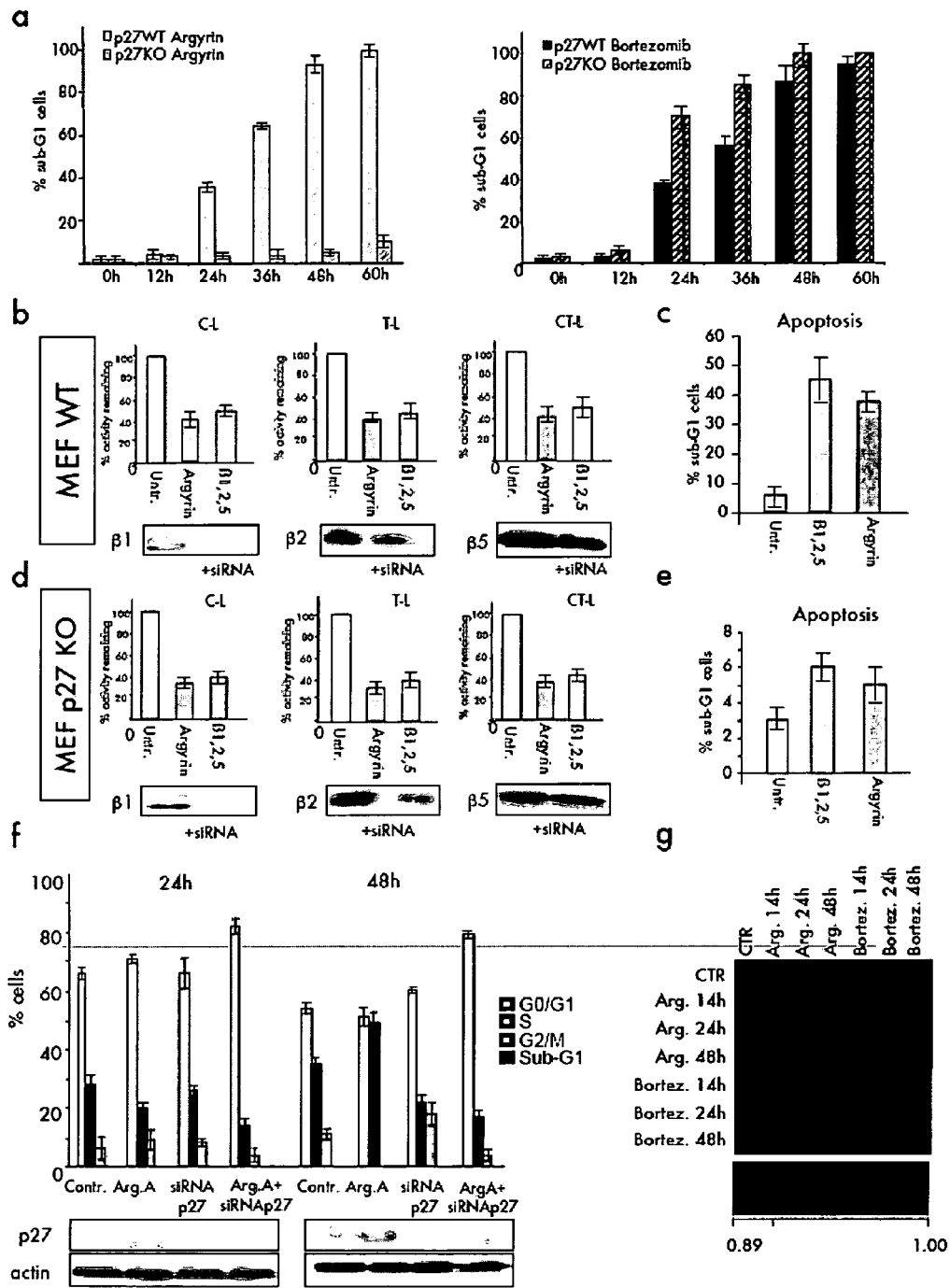
Figure 3:
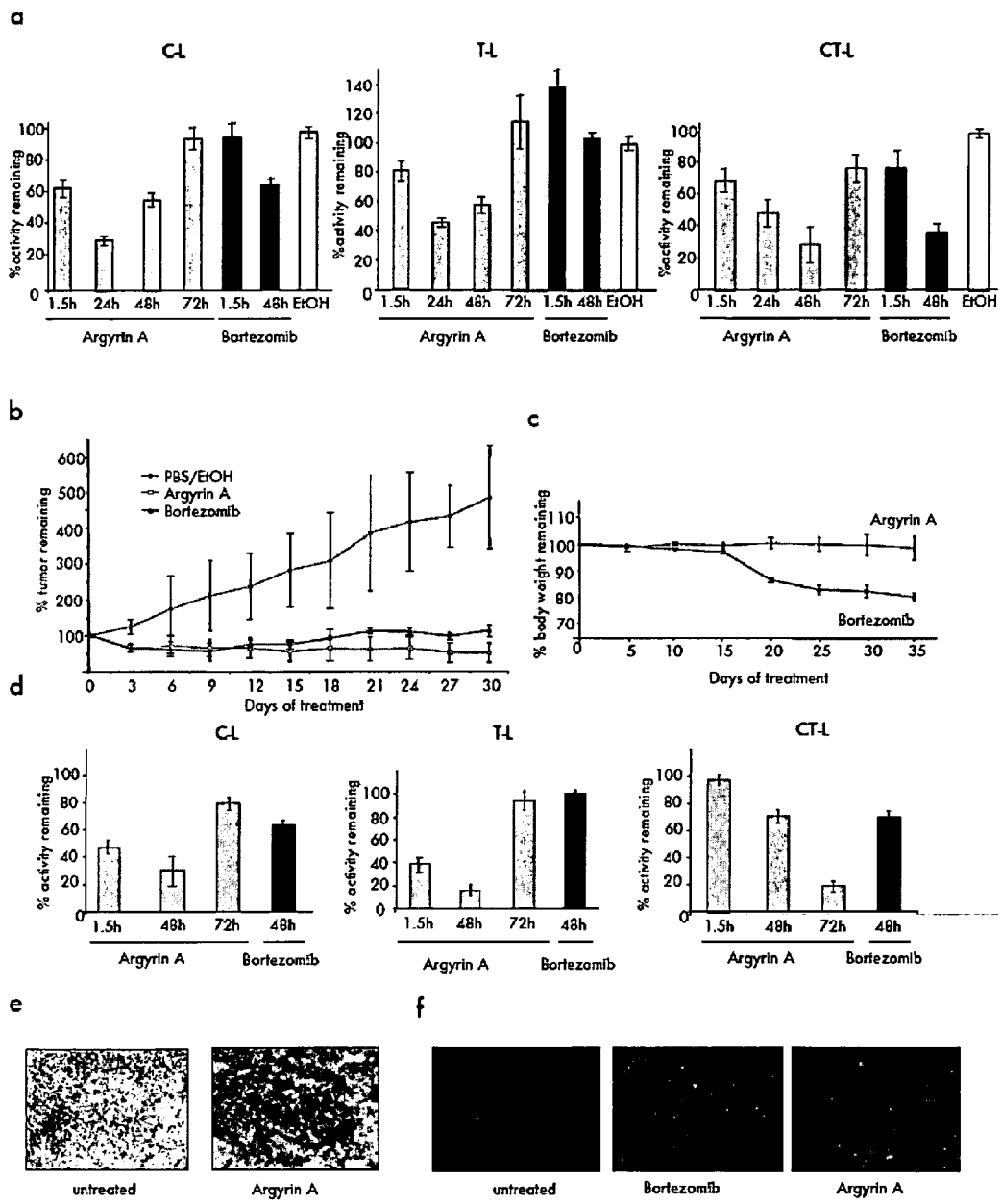
Figure 4:
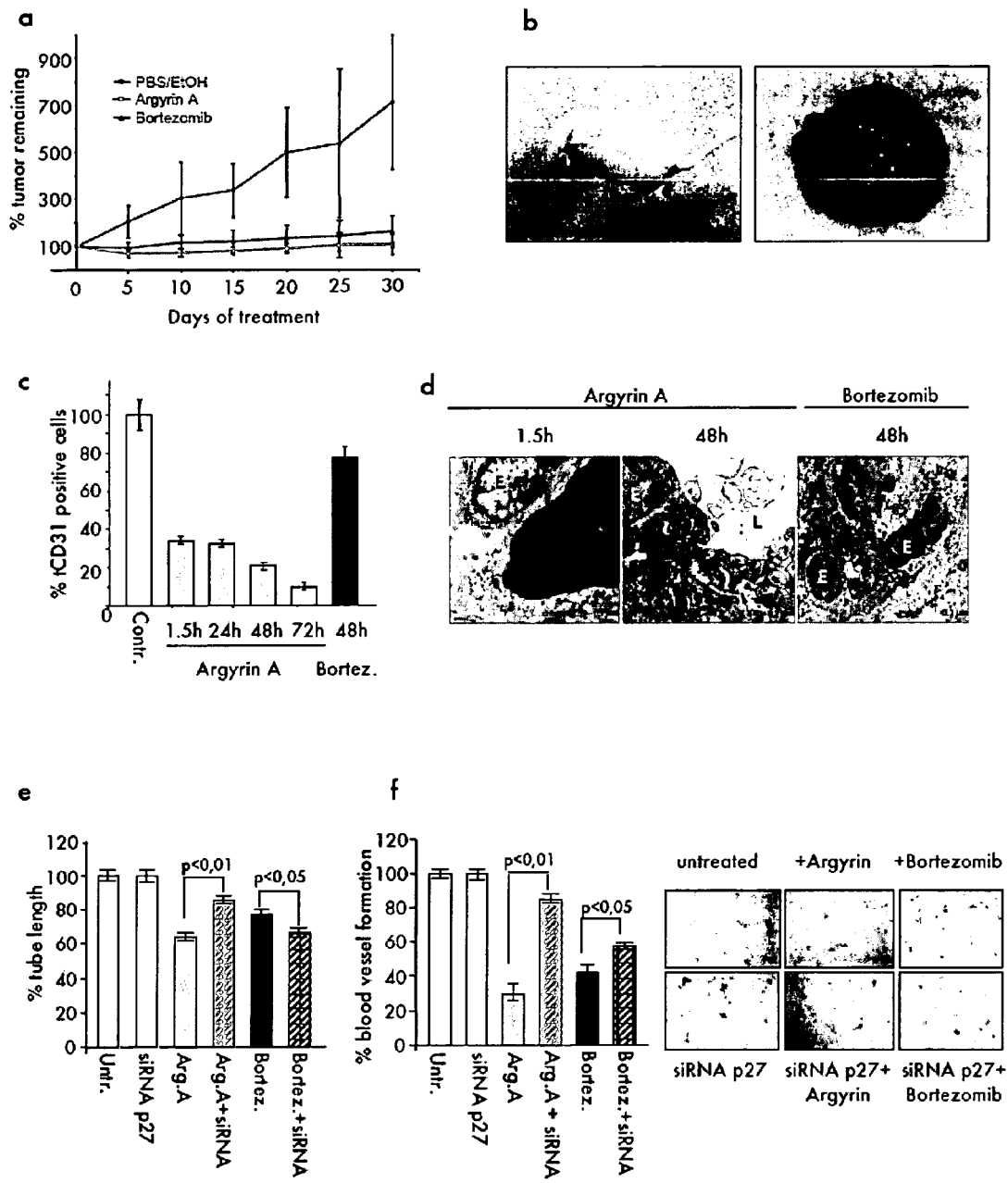
Figure 5:
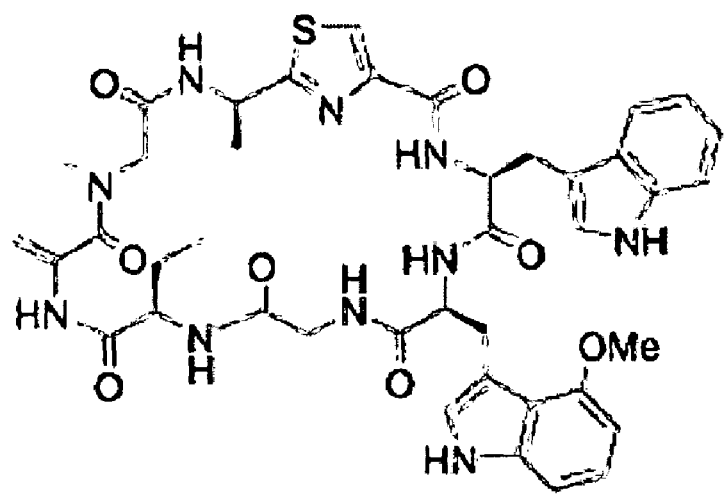
Figure 5:
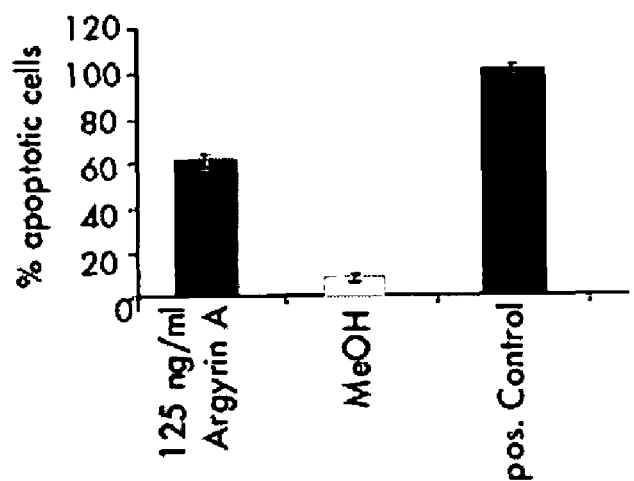
Figure 6:
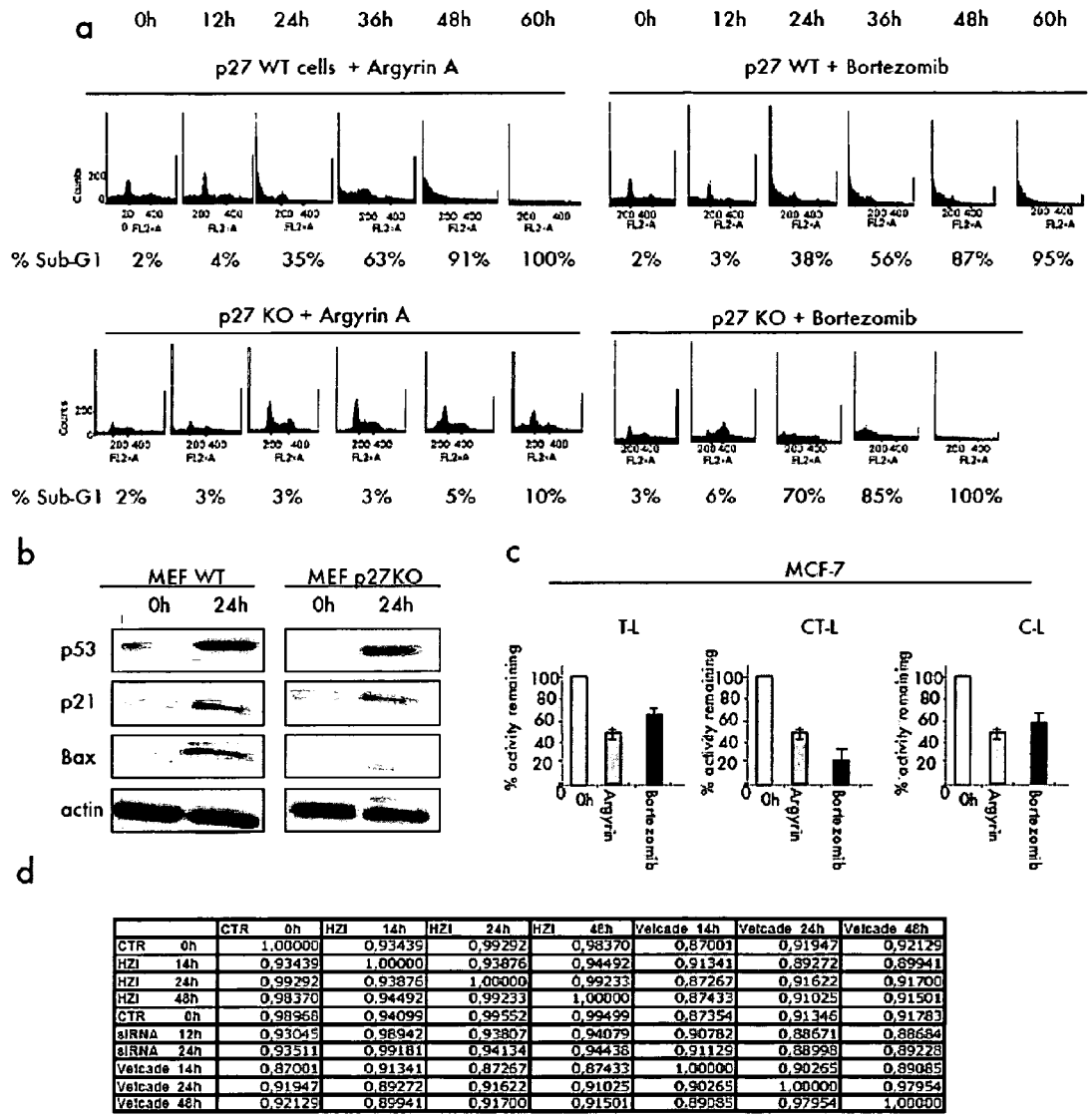
Figure 7:
FIG. 7 shows representative immunofluorescence co-stainings of endothelial cells in human colon cancer xenotransplanted tumors for CD31 and p27.
Figure 8:
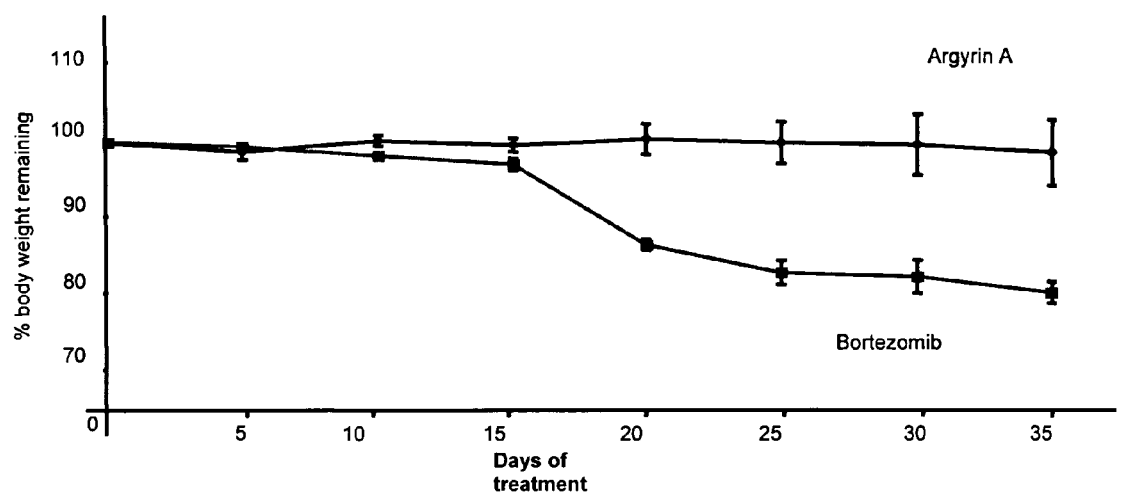
FIG. 8 shows that Argyrin A treatment is very well tolerated, as shown by the body weight of mice.

High Throughput Screen (HTS) for p27 Stabilizing Substances

A cellular high throughput screen for p27 stabilizing compounds was established by stably introducing a DNA plasmid (EGFP-N1, Clontech) which allows the expression of p27$^{kip1}$-GFP fusion protein in HeLa cells. p27-GFP expressing cells were selected with neomycin and several independent clones were subcultured. HeLa p27-GFP cells were seeded in 384 well plates (Corning) and incubated with a set of highly diverse natural products (part of the Helmholtz Center for Infection Research myxobacterial metabolite collection) at a concentration of 70 nM. GFP emission was determined by fluorometric measurements using a Victor 1420 multilabel counter (Perkin Elmer) at 3 h, 24 h, 48 h and 60 h after the start of treatment. The proteasome inhibitor MG132 was used as a positive control.

Cells and Tissue Culture

Primary human fibroblasts (HKI); HCT116 (colon cancer), MCF7 (breast cancer), CaCo (colon cancer), A549 (Lung cancer), HeLa (cervical cancer) and immortalized MEFs were cultivated in DMEM supplemented with 5% FCS and 2 mg/ml penicillin/streptomycin. SW480 cells (colon cancer) were cultivated in MC Coy's media supplemented with 5% FCS and 2 mg/ml penicillin/streptomycin.

Antibodies, Western Blotting, Immunofluorescence, Immunohistochemistry

Immunohistochemical staining of mouse tumour tissue, western Blotting and immunofluorescence experiments were done as previously described (Timmerbeul, I. et al. Testing the importance of p27 degradation by the SCFskp2 pathway in murine models of lung and colon cancer. *Proc Natl Acad Sci USA* 103, 14009-14 (2006). Kossatz, U. et al. C-terminal phosphorylation controls the stability and function of p27$^{kip1}$. *Embo J* 25, 5159-70 (2006).). The following antibodies were used: p27 (Cat. No. K25020-150; Transduction Labs), p21 (N20; Santa Cruz), p53 (FL-393; Santa Cruz), NfKB (C-20; Santa Cruz), Bax (P-19; Santa Cruz), Alexa fluor 488 (# A11001; Invitrogen), 20S-proteasome subunit beta 2 (Z) (PW9300; Bio-mol, for human cells), 20S-proteasome subunit beta 2 (Z) (PW8145; BIO TREND, for mouse cells); 20S proteasome subunit beta 1(Y) (PW8140; BIO TREND), 20S proteasome subunit beta 5 (PW8895; BIO TREND); PECAM Antibody clone MEC 13.3 (#550274; BD Pharmingen).

MTT Assays, Apoptosis, Flow Cytometry

MTT assays were done as previously described (Sasse, F. et al. Argyrins, immunosuppressive cyclic peptides from myxobacteria. I. Production, isolation, physico-chemical and biological properties. *J Antibiot (Tokyo)* 55, 543-51 (2002)). TUNEL staining of tissue sections was performed on 10 micrometer sections which were deparafinised and treated as recommended by the manufacturer. (In Situ Cell Death Detection Kit, Fluorescein; ROCHE, Cat #11 684 795 910). Flow cytometric analysis of cultured cells was done using a Becton Dickinson fluorescence cytometer as previously described (Malek, N. P. et al. A mouse knock-in model exposes sequential proteolytic pathways that regulate p27$^{Kip1}$ in G1 and S phase. *Nature* 413, 323-7 (2001)). Analysis of the distribution of cells in the cell cycle and the sub-G1 fraction was done using Cell Quest software. A histone-associated-DNA-fragments ELISA was used to determine the number of apoptotic cells according to manufacturers instructions (Roche #11 774425001).

siRNA siRNA knockdown was performed using transfection reagent FuGene6® or HiPerFect transfection reagent. Transfections were done using siRNA in a concentration of 0.2 nM for Psmb1, Psmb2, PSMB1, PSMB2 and CDKN1B and in a concentration of 0.4 nM for Psmb5 and PSMB5. All siRNA were purchased from Ambion.

```
p27 ID118714
p27 forward:
5'-CGUAAACAGCUCGAAUUAAtt-3'    (SEQ ID No. 1)

backward:
5'-UUAAUUCGAGCUGUUUACGtt-3'    (SEQ ID No. 2)

Psmb1: ID: 68878:
Psmb1 forward:
5'-GGAUUUUCAAUUCAUACCCtt-3'    (SEQ ID No. 3)

backward:
5'-GGGUAUGAAUUGAAAAUCCtt-3'    (SEQ ID No. 4)

Psmb2: ID70480:
Psmb2 forward:
5'-GGACGAUCAUGACAAGAUGtt-3'    (SEQ ID No. 5)
```

```
-continued
backward:
5'-CAUCUUGUCAUGAUCGUCCtt-3'      (SEQ ID No. 6)

Psmb5:ID 68783
Psmb5 forward:
5'-GGUGCUUAUAUUGCUUCCCtt-3'      (SEQ ID No. 7)

backward:
5'-GGGAAGCAAUAUAAGCACCtg-3'      (SEQ ID No. 8)

PSMB1: ID105612
PSMB1 forward:
5'-GACUGUCUUACGCUGACAAtt-3'      (SEQ ID No. 9)

backward:
5'-UUGUCAGCGUAAGACAGUCtc-3'      (SEQ ID No. 10)

PSMB2: ID: 105614
PSMB2 forward:
5'-GAUAUUACUCCUGUGUGUUtt-3'      (SEQ ID No. 11)

backward:
5'-AACACACAGGAGUAAUAUCtt-3'      (SEQ ID No. 12)

PSMB5: ID: 105622
PSMB5 forward:
5'-GAAGAGCCAGGAAUCGAAAtt-3'      (SEQ ID No. 13)

backward:
5'-UUUCGAUUCCUGGCCUUCtg-3'       (SEQ ID No. 14)
```

Proteasome Purification, Proteasome Assays

Proteasome assays with purified 20S proteasome were performed as previously described (Lightcap, E. S. et al. Proteasome inhibition measurements: clinical application. *Clin Chem* 46, 673-83 (2000)) using erythrocyte-derived 20S proteasome (Biomol International, #LP PW8720) and fluorometric substrates Succ-LLVY-AMC, BZ-VGR-AMC and Z-Lle-AMC (Biomol International, LP PW9905) as probes according to the manufacturers instructions. Proteasome extraction from cells and tumour sections was done as previously described (Crawford, L. J. et al. Comparative selectivity and specificity of the proteasome inhibitors BzLLLCOCHO, PS-341, and MG-132. *Cancer Res* 66, 6379-86 (2006)). Briefly cells (MEF or MCF-7) or tissue sample homogenate (tumour sections) were re-suspended in 1 mL ATP/DTT lysis buffer (10 mmol/L Tris-HCl (pH 7.8), 5 mmol/L ATP, 0.5 mmol/L DTT, 5 mmol/L $MgCl_2$), and incubated on ice for 10 minutes, followed by sonication for 15 seconds. The lysates were centrifuged at 400×g for 10 min at 4° C., and the resulting supernatant containing proteasomes was stable at −80° C. with the addition of 20% glycerol for at least 1 month. Protein concentration of the samples was measured using a coomassie protein assay (Pierce, Rockford, Ill.).

For proteasome extraction from whole blood, frozen whole blood cell pellets were thawed and lysed in 2-3 pellet volumes cold lysis buffer (5 mM EDTA, pH 8.0). Lysates were spun down at 4° C. and the supernatant was transferred to a fresh tube. 5 μl was taken for the determination of protein concentration using a coomassie protein assay (Pierce, Rockford, Ill.).

Proteasome assays using proteasome purified from cells or tissues were carried out in a 100 μL reaction volume containing 20 μg proteasome extract, 50 mmol/L EDTA and 60 μmol/L fluorogenic substrate (chymotrypsin-like (CT-L), trypsin-like (T-L) or caspase-like (C-L)) in ATP/DTT lysis buffer at 37° C. The assay buffer was supplemented with a final concentration of 0.05% SDS for the evaluation of the chymotrypsin-like activity and caspase-like activity. The rate of cleavage of fluorogenic peptide substrates was determined by monitoring the fluorescence of released amonomethylcoumarin using a Victor 1420 Multilabel counter (Wallac) at an excitation wavelength of 395 nm and emission wavelength of 460 nm over a period of 60 min.

HMVEC Culture, In Vitro Capillary-Like Tube Structure Formation Assay and Immunofluorescence Primary microvascular endothelial cells (HMVEC) were isolated from human foreskin. The cells were kept at 37° C. and 10% CO2 in EGM-2 MV from Cambrex which includes the basal medium (EBM-2), FBS, hydrocortisone, hFGF-B, VEGF, R3-IGF, ascorbic acid, hEGF, gentamicin and amphotericin. The effect of argyrin A or bortezomib on in vitro angiogenesis was determined by matrigel capillary-like tube structure formation assay. To examine the effect of the different compounds on in vitro angiogenesis, HMVECs were seeded in 96-well culture plates precoated with Matrigel (BD Biosciences, #354248) and exposed to argyrin A or bortezomib. Enclosed networks of tube structures from three randomly chosen fields were scored under the microscope (Leica, Cambridge, United Kingdom). Pictures were taken with an Axio Vision 3.1 Zeiss camera and scored by determining tube length and the formation of closed vessel like structures.

Xenotransplant Studies

1×107 SW480 cells or HCT116 cells (in 100 microliters DMEM medium and 100 microliters matrigel) were s.c. injected into the flanks of NMRI nu/nu mice. Tumours grew for approx. 18 days until they reached appropriate size (200 mm3). Tumour size was measured with a digital calliper and calculated with the help of the following formula: (Length× width2)*π/6. All experiments were done after review and in accordance with the animal rights and protection agencies of Lower Saxony, Germany.

EM

Small specimens of the tumour were fixed in 2.5% glutaraldehyde (Polysciences, Warrington, Pa., USA) in 0.1 M sodium cacodylate, pH 7.3 and postfixed with 2% osmium tetroxide (Polysciences) in the same buffer. After dehydration in graded alcohols they were embedded in Epon (Serva, Heidelberg, Germany). Thin sections stained with uranyl acetate and lead citrate were examined in a Philips EM 301 electron microscope. The electron micrographs were selected, digitalized, and processed using Adobe Photoshop 6.0.

DNA Microarray Hybridization and Analysis.

Quality and integrity of the total RNA isolated was controlled by running all samples on an Agilent Technologies 2100 Bioanalyzer (Agilent Technologies; Waldbronn, Germany). For biotin-labelled target synthesis starting from 3 μg of total RNA, reactions were performed using standard protocols supplied by the manufacturer (Affymetrix; Santa Clara, Calif.). In each case 10 μg of labelled cRNA were hybridized to an identical lot of Affymetrix GeneChips HG-U133 2.0 for 16 hours at 45° C. After hybridisation the GeneChips were washed, stained with SA-PE and read using an Affymetrix GeneChip fluidic station and scanner.

Data Analysis

Analysis of microarray data was performed using the Affymetrix GCOS 1.2 software. For normalization all array experiments were scaled to a target intensity of 150, otherwise using the default values of GCOS 1.2. The entire data set was deposited on the public GEO database server in a MIAME compliant format and is available under accession no. GSE8565. The correlation coefficient for a pair of arrays was defined as $$\sum_i [(a_i - \mu_a) * (b_i - \mu_b)]/n(\sigma_a * \sigma_b)$$

where ai are the signals in array a, bi are the signals in array β, μ, and σ are the respective means and standard deviations, and n is the number of items in each array. Functional clustering based on gene ontology terms were performed using Array Assist 5.1 (Stratagene, La Jolla, Calif.).

Statistical Analysis

Statistical analysis was carried out using Microsoft Excel software. If not stated otherwise, all data are presented as mean+/− SD (error bars represent SD in all figures). Inter-group comparisons were performed by two-tailed student t test. Probability values of p<0.05 were interpreted to denote statistical significance.

Generation of p27-GFP-Cell Line as Reporter Construct

Human p27cDNA (in plasmid vector CS2+) was digested with EcoR1 and BamH1, and the resulting fragment was ligated after gel purification into the vector pEGFP-N1 (Clontech) that was cut with the same restriction enzymes. Thus, a reading frame shift fusion with the GFP as contained in the pEGFP-vector was generated. The plasmid was then transfected into Hela cells, and, following selection of the cells with kanamycin, cellular clones were isolated which had the plasmid integrated stably into their chromosome. The expression of the p27EGFP proteins was confirmed using Western blots and immune precipitations for both p27 and GFP.

Effect of Different Argyrin-Derivatives

The following table summarizes the effects of argyrin-derivatives A to H on two cancer cell lines, H15 (cervix carcinoma) and SW-480 (colon cancer). In order to test the efficacy, a p27-GFP-clone was used.

Effect of Different Argyrin-Derivatives

| Argyrin | Mean of FSC-H (Log)* H15 p27-GFP-clone | MIC (visual)** [μg/ml] H15 | MIC (visual)** [μg/ml] SW-480 | IC-50*** [μg/ml] SW-480 |
|---|---|---|---|---|
| A | 8.52 | 4 | 4 | Ca. 0.05 |
| B | 7.60 | 12 | 12 | Ca. 0.05 |
| C | 7.36 | 37 | 37 | Ca. 0.05 |
| D | 7.69 | 12 | 37 | Ca. 0.05 |
| E | 8.52 | 4 | 4 | 0.7 |
| F | 11.24 | 0.5 | 0.2 | 0.05 |
| H | | 37 | 37 | Ca. 0.5 |

*The GFP-fluorescence was determined per FACS after a 24 h incubation of the clone H15GFP-p27 (HeLa-cell line; cervix-carcinoma) with the different argyrin-derivatives (500 ng/ml).
**Minimal concentration of a serial dilution exhibiting a visual effect.
***Half-maximal inhibition of the proliferation of SW-480 (colon cancer cell line; analysis following an MTT-test). Since all derivatives with the exception of E and F show a biphasic progression of inhibition with a plateau at 50% inhibition, the determination of an IC-50-value is difficult. It can be seen that argyrin F is particularly effective and thus preferred.

The invention claimed is:

1. A method of treating cancer, wherein the cancer is one that can be treated by inhibiting the degradation of p27, wherein said method comprises administering to a subject suffering from said cancer an effective amount of a compound of formula I:

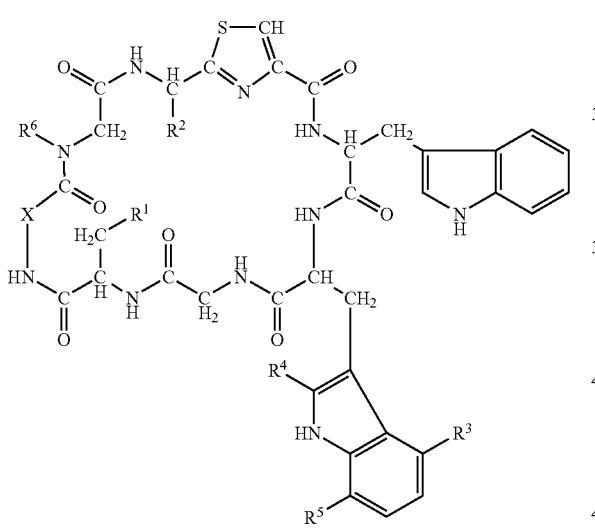

(formula I)

wherein
- $R^1$ and $R^2$ independently are hydrogen, $C_1$-$C_4$ alkyl which is unsubstituted or substituted by OH, or $C_1$-$C_4$ alkoxy;
- $R^3$ is hydrogen, $C_1$-$C_8$ alkyl which is unsubstituted or substituted by OH or OR, wherein R is selected from hydrogen, $C_1$-$C_4$ alkyl, aryl or acetyl,
- $R^4$ is hydrogen, halogen, $C_1$-$C_4$ alkyl which is unsubstituted or substituted by OH, or $C_1$-$C_4$ alkoxy;
- $R^5$ is hydrogen or halogen;
- $R^6$ is hydrogen or $C_1$-$C_4$ alkyl; and
- X is C=$CH_2$ or $CHR^7$ wherein $R^7$ is $C_1$-$C_4$ alkyl which is unsubstituted or substituted by —S—$C_1$-$C_4$ alkyl, and pharmaceutically acceptable salts thereof, and wherein the administration of said compound results in stabilization and/or inhibition of the degradation of p27, thereby treating the cancer.

2. The method, according to claim 1, wherein
$R^1$, $R^2$, and $R^3$ independently are hydrogen, $C_1$-$C_4$ alkyl which is unsubstituted or substituted by OH, or $C_1$-$C_4$ alkoxy;
- $R^4$ is hydrogen, halogen, $C_1$-$C_4$ alkyl which is unsubstituted or substituted by OH, or $C_1$-$C_4$ alkoxy;
- $R^5$ is hydrogen or halogen;
- $R^6$ is hydrogen or $C_1$-$C_4$ alkyl; and
- X is C=$CH_2$ or $CHR^7$ wherein $R^7$ is $C_1$-$C_4$ alkyl which is unsubstituted or substituted by —S—$C_1$-$C_4$ alkyl, and pharmaceutically acceptable salts thereof.

3. The method, according to claim 1, wherein
- $R^1$ is hydrogen or unsubstituted $C_1$-$C_4$ alkyl;
- $R^2$ is hydrogen or $C_1$-$C_4$ alkyl which is unsubstituted or substituted by OH;
- $R^3$ is hydrogen or $C_1$-$C_4$ alkoxy;
- $R^4$ is hydrogen or unsubstituted $C_1$-$C_4$ alkyl;
- $R^5$ is hydrogen or bromo;
- $R^6$ is hydrogen or methyl; and
- X is C=$CH_2$ or $CHR^7$ wherein $R^7$ is methyl which is unsubstituted or substituted by —S-ethyl,
and pharmaceutically acceptable salts thereof.

4. The method according to claim 1, wherein
- $R^1$ is hydrogen or methyl;
- $R^2$ is methyl or hydroxymethyl;
- $R^3$ is hydrogen or methoxy;
- $R^4$ is hydrogen or methyl;
- $R^5$ is hydrogen;
- $R^6$ is methyl; and
- X is C=$CH_2$,
and pharmaceutically acceptable salts thereof.

5. The method, according to claim 1, wherein the compound has the following formula

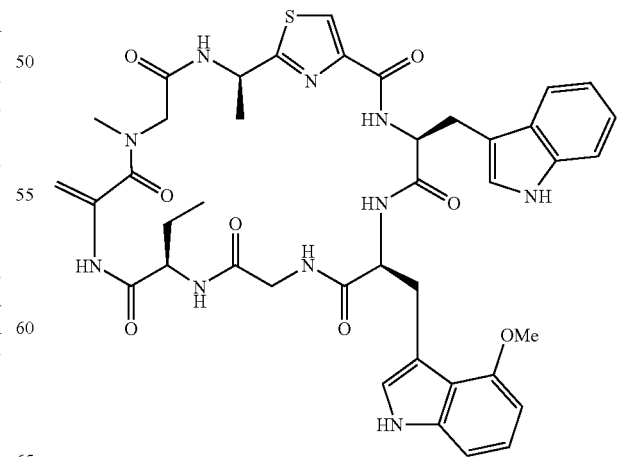

and pharmaceutically acceptable salts thereof.

6. The method, according to claim 1, wherein the subject is a mammal.

7. The method, according to claim 1, wherein the treatment comprises blocking tumor cell growth, blocking, and/or destroying existing tumour vasculature, treatment of breast cancer, treatment of hepatocellular carcinoma, treatment of cervix carcinoma, treatment of lung carcinoma, treatment of multiple myeloma, and/or treatment of colon cancer.

8. The method, according to claim 1, which further comprises the administration of additional pharmaceutically active anti-tumor ingredients.

9. The method, according to claim 1, wherein the compound is administered at a dose of 0.01 mg to 200 mg/kg.

10. The method according to claim 1, wherein the compound is selected from argyrin A, argyrin F, and pharmaceutically acceptable salts thereof.

11. The method according to claim 6, wherein the subject is a human.

12. The method according to claim 1, which further comprises the administration of paclitaxel and/or bortezomib.

* * * * *

UNITED STATES PATENT AND TRADEMARK OFFICE
CERTIFICATE OF CORRECTION

PATENT NO.        : 8,217,071 B2
APPLICATION NO.   : 12/527428
DATED             : July 10, 2012
INVENTOR(S)       : Nisar Malek et al.

It is certified that error appears in the above-identified patent and that said Letters Patent is hereby corrected as shown below:

<u>Column 2,</u>
Line 62, "p2'7," should read --p27,--

<u>Column 11,</u>
Line 20, "xenotrans-planted" should read --xenotransplanted--

Signed and Sealed this
Twenty-fifth Day of September, 2012

David J. Kappos
*Director of the United States Patent and Trademark Office*